United States Patent

Frigo

(10) Patent No.: US 9,297,758 B2
(45) Date of Patent: Mar. 29, 2016

(54) VARIABLE GEOMETRY OPTICAL GAS DETECTOR

(71) Applicant: N.E.T. SRL, Cornaredo (MI) (IT)

(72) Inventor: Giacomino Frigo, Cornaredo (IT)

(73) Assignee: N.E.T. SRL, Cornaredo (MI) (IT)

( * ) Notice: Subject to any disclaimer, the term of this patent is extended or adjusted under 35 U.S.C. 154(b) by 5 days.

(21) Appl. No.: 14/219,631

(22) Filed: Mar. 19, 2014

(65) Prior Publication Data

US 2014/0291525 A1   Oct. 2, 2014

(30) Foreign Application Priority Data

Mar. 29, 2013   (IT) .............................. MI2013A0478

(51) Int. Cl.
*G01N 21/61* (2006.01)
*G01N 21/3504* (2014.01)
*G01N 21/03* (2006.01)

(52) U.S. Cl.
CPC ............ *G01N 21/61* (2013.01); *G01N 21/0303* (2013.01); *G01N 21/3504* (2013.01); *G01N 2021/036* (2013.01); *G01N 2021/0307* (2013.01); *G01N 2021/0378* (2013.01)

(58) Field of Classification Search
CPC .................................... G01J 5/00; G01N 21/61
USPC .................................. 250/343, 349, 345, 344
See application file for complete search history.

(56) References Cited

U.S. PATENT DOCUMENTS

| | | | | |
|---|---|---|---|---|
| 4,271,360 A | * | 6/1981 | Ward ..................... | G08B 17/12 250/338.1 |
| 4,700,079 A | * | 10/1987 | Ito ........................ | G08B 17/103 250/574 |
| 4,707,604 A | * | 11/1987 | Guscott ................ | G08B 13/193 250/342 |
| 4,709,152 A | * | 11/1987 | Muller .................. | G08B 13/193 250/342 |
| 4,920,268 A | * | 4/1990 | Walters ................ | G08B 13/193 250/342 |

(Continued)

FOREIGN PATENT DOCUMENTS

| | | |
|---|---|---|
| EP | 0 647 845 A1 | 4/1995 |
| EP | 1 972 923 A2 | 9/2008 |

(Continued)

OTHER PUBLICATIONS

Search Report and Written Opinion completed Dec. 13, 2013 by the European Patent Office in priority Italian application No. IT MI2013A000478.

*Primary Examiner* — David Porta
*Assistant Examiner* — Djura Malevic
(74) *Attorney, Agent, or Firm* — Abelman, Frayne & Schwab (57) ABSTRACT

An optical gas detector (20) in metal or other suitable material, comprising a cup-shaped body (1), with upper mouth (9) closed by a lid (2) the bottom of which (8) is flat and provided with a plurality of through holes (15) variously arranged, which place said detector (20) in communication with the outside environment, and inside which an IR source (10) and an IR analyser (11) are placed, borne by an overlying circuit board (12). The inner lateral surface of the body (1) forming a first reflector wall (6) having a regular or irregular annular extension and defining, in conjunction with a second convex or concave reflector wall (7, 7') of a shaped appendage (5) and with one or more reflectors (3, 3', 21, 22, 23,24,25) preinserted and positioned in the body (1), a multiplicity of geometrically alternative optical paths (4, 4', 4", 4''') of the electromagnetic radiation emitted by the IR source (10) and detected by the IR analyser (11).

9 Claims, 7 Drawing Sheets

(56) References Cited

U.S. PATENT DOCUMENTS

| | | | | |
|---|---|---|---|---|
| 5,546,074 | A * | 8/1996 | Bernal | G08B 17/107 |
| | | | | 250/574 |
| 5,601,693 | A * | 2/1997 | Davies | 204/400 |
| 5,721,430 | A * | 2/1998 | Wong | G01N 21/3518 |
| | | | | 250/338.5 |
| 5,734,165 | A * | 3/1998 | Unal | G01N 21/031 |
| | | | | 250/338.1 |
| 6,016,203 | A * | 1/2000 | Martin | 356/432 |
| 6,455,854 | B1 | 9/2002 | Richman | |
| 6,469,303 | B1 * | 10/2002 | Sun et al. | 250/343 |
| 6,753,967 | B2 * | 6/2004 | Stuttard | G01N 21/0303 |
| | | | | 250/343 |
| 6,989,549 | B2 * | 1/2006 | Diekmann | G01N 21/3504 |
| | | | | 250/343 |
| 7,244,939 | B2 * | 7/2007 | Stuttard | 250/343 |
| 7,488,942 | B2 * | 2/2009 | Hopkins | G01N 21/031 |
| | | | | 250/343 |
| 7,535,007 | B1 | 5/2009 | Freeman et al. | |
| 8,193,502 | B2 * | 6/2012 | Hodgkinson | G01N 21/0303 |
| | | | | 250/339.12 |
| 9,035,256 | B2 * | 5/2015 | Gibson | G01N 21/3504 |
| | | | | 250/343 |
| 2002/0063216 | A1 * | 5/2002 | Clausen et al. | 250/343 |
| 2004/0007667 | A1 * | 1/2004 | Diekmann et al. | 250/343 |
| 2006/0086903 | A1 * | 4/2006 | Hopkins | G01N 21/031 |
| | | | | 250/339.13 |
| 2006/0138328 | A1 * | 6/2006 | Hopkins | G01N 21/0303 |
| | | | | 250/339.13 |
| 2006/0226367 | A1 * | 10/2006 | Hopkins | G01N 21/031 |
| | | | | 250/343 |
| 2009/0235720 | A1 * | 9/2009 | Smith | G01J 3/02 |
| | | | | 73/31.05 |
| 2010/0283991 | A1 * | 11/2010 | Chrzan | G01N 21/09 |
| | | | | 356/51 |
| 2011/0031402 | A1 * | 2/2011 | Huttmann et al. | 250/340 |
| 2012/0112073 | A1 * | 5/2012 | Bachels | G08B 13/193 |
| | | | | 250/353 |
| 2013/0075615 | A1 * | 3/2013 | Starta | G01N 21/3504 |
| | | | | 250/341.7 |

FOREIGN PATENT DOCUMENTS

| | | |
|---|---|---|
| GB | 2 316 712 | 3/1998 |
| GB | 2 317 010 | 3/1998 |
| GB | 2 353 591 | 2/2001 |
| GB | 2 368 392 | 5/2002 |
| GB | 2 369 884 | 6/2002 |
| GB | 2 372 099 | 8/2002 |
| GB | 2 396 405 | 6/2004 |
| GB | 2 401 432 | 11/2004 |
| GB | 2 449 433 | 11/2008 |
| JP | 2008145292 | 6/2008 |

* cited by examiner

VARIABLE GEOMETRY OPTICAL GAS DETECTOR

CROSS-REFERENCE TO RELATED APPLICATION

This application claims priority to Italian Application No. MI2013A000478, filed Mar. 29, 2013, the disclosure of which is incorporated by reference herein in its entirety and made a part of this application.

BACKGROUND OF THE INVENTION

1. Field of the Invention

The present invention relates to a variable geometry optical gas detector. More specifically, the present invention relates to a gas detector of the non-dispersive optical type in which the electromagnetic radiation in the infrared band is emitted by a source for the purpose and channelled to an analyser through an optical path of variable geometry and configurable depending on the nature of the gas to be detected.

2. Description of the Related Art

In the prior art, detectors of gaseous substances are known of which function on the optical spectrophotometry principle by means of dispersive and non-dispersive sensors. These sensors detect the absorption of part of the electromagnetic radiation emitted by a source, passing through a gaseous substance appropriately interposed between said source and an analyser. The variation in the beam of electromagnetic radiation, due to the quantity of radiation absorbed by the gaseous substance, determines the nature and quantity of the latter.

The present invention relates to non-dispersive optical gas detectors which use electromagnetic radiation in the infrared band (NDIR Non Dispersive Infra Red). However, the same solution is also applicable to dispersion sensors and to sensors based on the absorption of electromagnetic radiation having wavelengths different from infrared.

The NDIR sensors detect the attenuation of the infrared (IR) luminous radiation caused by a target gas present in a gas sample. The degree of attenuation is a function of the absorption wavelength of the IR radiation, of the length of the optical path covered by the same, of the nature and concentration of the target gas present along said optical path and of the wavelength of the electromagnetic radiation detected by the analyser.

Normally the light source is provided by means of a filament bulb and the analyser by a pyroelectric sensor or by a thermopile.

It is also known that the level of sensitivity and accuracy of the detector is proportional to the length of the optical path between the source and analyser but it is desirable, for reasons of space and standard applications, to make a detector of reduced, compact dimensions.

It is, furthermore, advantageous to minimise the distance across which the gas is diffused to reach the optical path, so as to minimise the detection times of the detector.

Many examples of detectors are present in the state of the art and on the market. In general, NDIR detectors comprise a source of radiation, an analyser sensitive to the radiation emitted and an optical path which the radiation moves along in the passage from the source to the analyser. These detectors are also provided with means for allowing a sample gas, containing the target gas, to be introduced along the optical path. Said means may be passive, for example, holes through which the sample gas may spread, or active, for example micro pumps.

The analyser measures the intensity of the radiation of one or more wavelengths determined and corresponding to the absorption bands of the target gas and produces an electric measurement signal. Generally, said electric measurement signal in output from the analyser is compared to a reference signal relative to the intensity of the radiation on several wavelengths which are not absorbed by the target gas.

Some technical solutions for these NDIR detectors are described in the patents GB 2,317,010 and GB 2,368, 392. These embodiments use a tube as the optical path, with the source and analyser placed at ends of said tube, and means to allow the flow of sample gas through said tube.

Some solutions, described in GB 2,353,591 and U.S. Pat. No. 6,455,854 refer to detectors of larger dimensions which form an open optical path (without a tube) with the source and the analyser again placed at the ends of said optical path. All these types of detectors have the drawback however of being cumbersome and not utilisable where compact forms and dimensions are required.

The patent GB 2,396,405 describes a detector with a relatively long optical path, placed in a space limited by means of grooves which define a flat spiral path or thread. The source and the analyser are always placed at the ends of the optical path.

Other patents, such as GB 2,401,432, GB 2,372,099 and GB 2,369,884 describe detectors which use circular/spherical paths of compact dimensions and elements having optically fixed reflector surfaces such as in JP 2008 145292 and GB 2,316,172, again made with limited spaces and with the source and the analyser positioned at the end of the optical path and where, in the case of JP 2008 145292 the radiation is aimed towards the analyser at various angled trajectories. Especially in the case of GB 2,449,433, the optical path develops on two superposed levels and the optical radiation is deviated by appropriate means from one level to the other.

The typical drawback of this latter type of embodiment relates to the fact that the luminous radiation, not following a rectilinear path and on various levels, is considerably attenuated due to the refraction thereof on the delimiting and/or reflector surfaces of the optical path.

A further drawback of these detectors relates to the fact of not being adaptable to the various types of gas since each sensor has a fixed optical path with a specific length for a certain type of gas.

SUMMARY OF THE INVENTION

The purpose of the present invention is to overcome the drawbacks complained of above.

More specifically, the purpose of the present invention is to provide a variable geometry optical gas detector able to guarantee a high degree of accuracy as regards determining the quality and quantity of gas.

A further purpose of the invention is to provide a variable geometry optical gas detector which permits alternative optical paths to be realised configurable at the moment of construction and assembly of said detector depending on the nature of the gas to be identified.

A further purpose of the invention is to make available to users a variable geometry optical gas detector suitable for ensuring a high level of resistance and reliability over time, in addition such as to be easy and economical to produce.

These and other purposes are achieved by the variable geometry optical gas detector which the present invention relates to and according to the main claim.

BRIEF DESCRIPTION OF THE DRAWINGS

The construction and functional characteristics of the variable geometry optical gas detector of the present invention will be more clearly comprehensible from the detailed description below in which reference is made to the appended drawings which show a preferred and non-limiting embodiment with some variants, and wherein:

FIG. 1 is an exploded, schematic, axonometric view partially in cross-section, of the detector which the present invention relates to;

FIGS. 2a and 2b are schematic, axonometric views partially in cross-section, of two different optical path geometries realisable within the detector which the invention relates to;

FIGS. 4a and 4b are schematic, plan views of possible configurations of the optical path made inside the detector which the invention relates to;

DETAILED DESCRIPTION OF THE PREFERRED EMBODIMENTS

Figure 1:
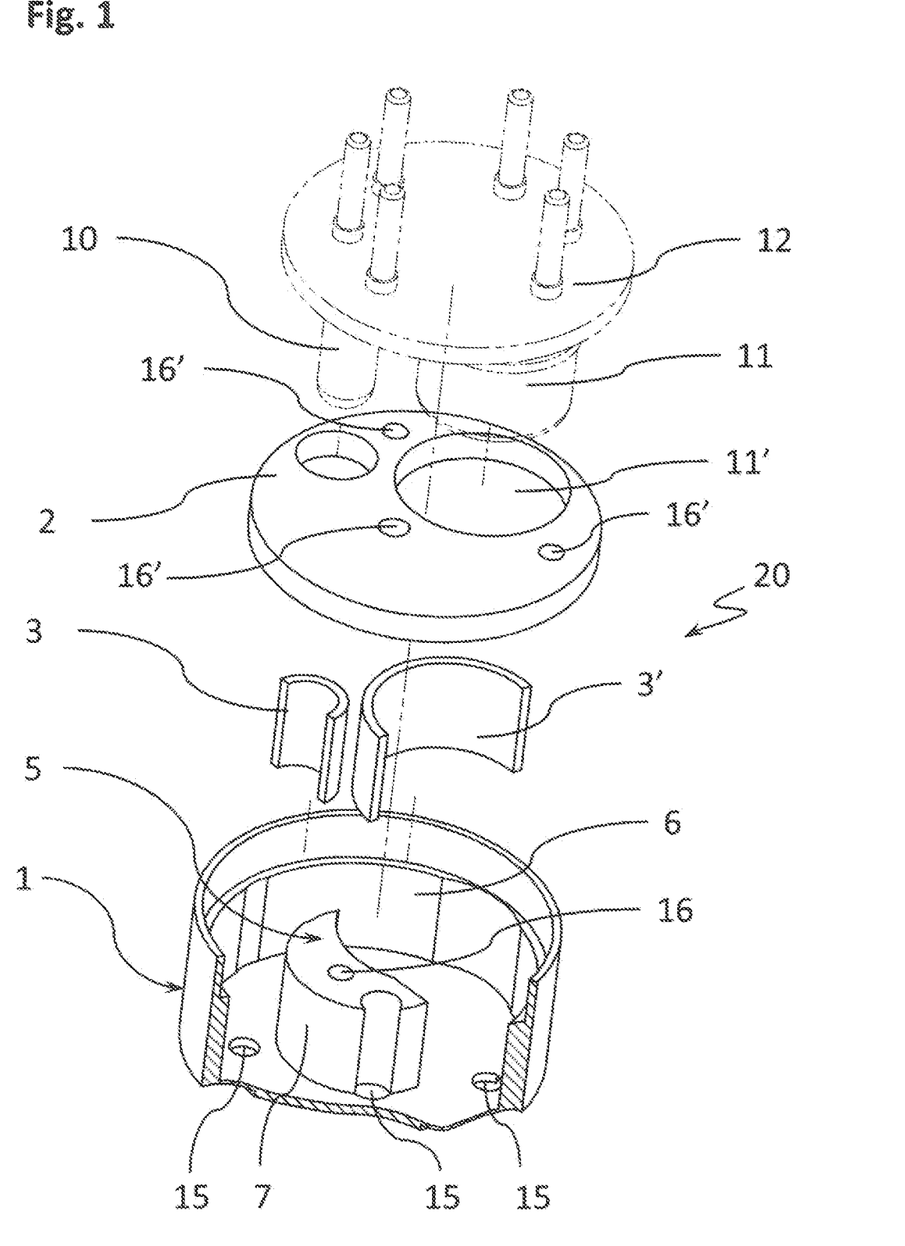
Figure 2A:
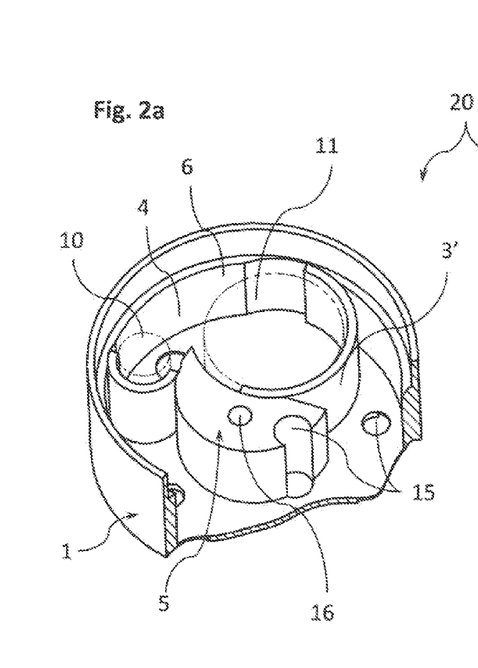
Figure 2B:
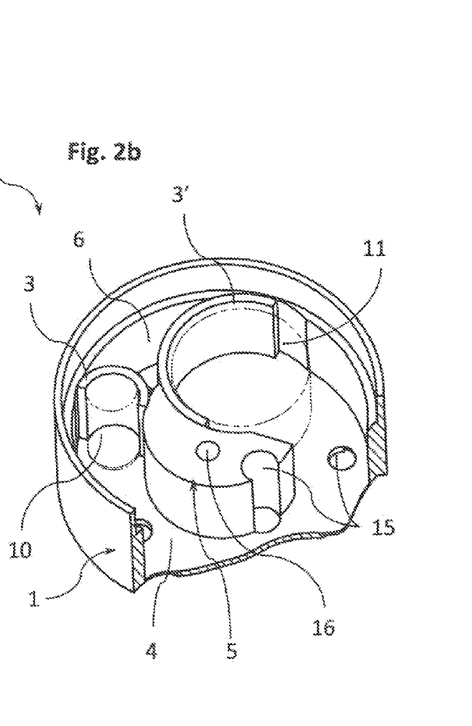

With initial reference to FIGS. 1, 2a and 2b, the variable geometry optical gas detector according to the present invention, globally denoted by reference numeral 20 and the optical part only of which is shown by way of example in FIGS. 2a and 2b, consists in its more general form of a cup-shaped body 1, surmounted by a disc-shaped lid 2. Said lid 2, shown in schematic form in FIG. 1, is provided with through apertures 10' and 11' in which an IR source 10 and an IR analyser 11 of the known type are inserted entirely or in part, borne by a circuit board; said circuit board 12, equally known, is attached with screws or equivalent means to the lid 2. Said IR analyser 11 and IR source 10 extend partially inside the body 1, after the lid 2 and the circuit board 12 have been coupled to said body 1.

According to the invention, the body 1 defines the seat for one or more reflectors 3 and 3', shaped so as to optimally deviate and reflect the electromagnetic radiation emitted by the IR source.

Figure 3A:
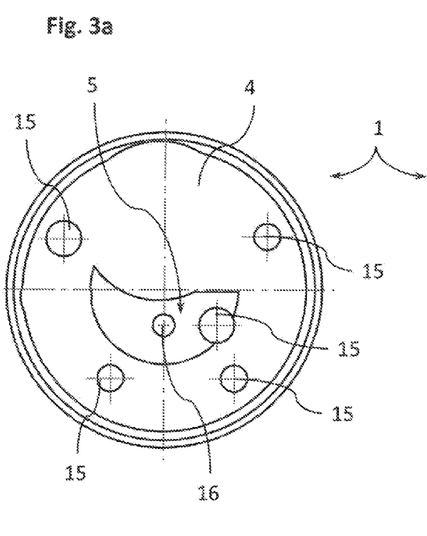
FIGS. 3a and 3b show a schematic, plan view and an axonometric view, partially in cross-section, of the body of the detector.
Figure 3B:
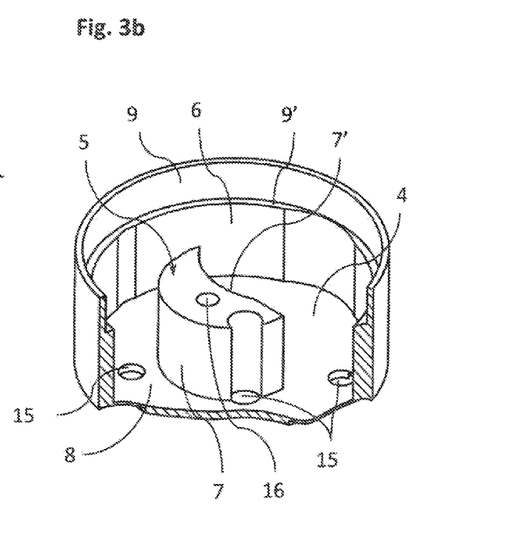

With further reference to FIGS. 3a and 3b, an optical path 4 is made in the body 1 in combination with a shaped appendage 5 which projects in a substantially central position and is composed of a tower comprising convex 7 and concave walls 7', delimited in a radial outward direction by the reflector wall 6, with mirrored finish, which corresponds to the inner lateral wall of said body 1 and defines a regular annular extension; the optical path 4 is instead defined inwards by the convex wall of the outer surface of the shaped appendage 5. Said optical path 4 is closed above and below by the lid 2 and by the bottom of the body 1, indicated by reference numeral 8 in FIG. 3b.

The coupling between the body 1 and the lid 2 is made by means of screws or equivalent means inserted in the holes 16. At the mouth 9 of the body 1 the lid 2 abuts at a recess 9' extending annularly in the body 1 and constituting the upper rim of the reflector wall 6, as in FIG. 3b.

As shown in FIGS. 1 to 4d, multiple through holes 15 suitable for placing the optical path 4 in communication with the outside environment and holes 16 for housing screws are made on the body 1. Holes 16' for housing the screws attaching the various components to each other are also present on the lid 2, shown in schematic form in FIG. 1.

Figure 7A:
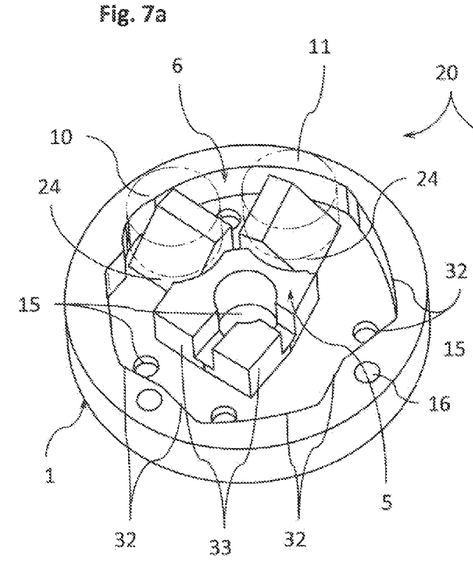
FIGS. 7a and 7b are schematic, axonometric views of two further geometries of optical path made according to other different embodiments.
Figure 7B:
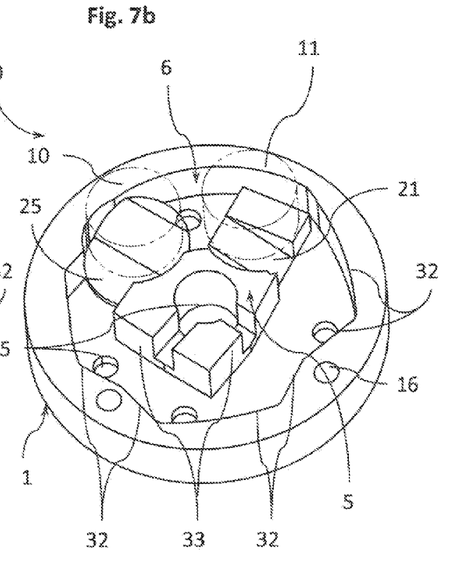

With reference to FIGS. 1, 2a, 2b and 3b, the reflector wall 6 which delimits the optical path 4 has a regular circular extension, or with reference to FIGS. 7a and 7b, an irregular annular extension, where said reflector wall 6, equally having a minor finish, is formed of a succession of sections 32 having a mixed linear extension and/or arched sectors having a concave or convex extension.

Housings or references, not shown, are also made in the body 1, suitable for the attachment in alternative positions of the reflector elements or reflectors 3 and 3' having the function of deflecting the electromagnetic radiation coming from the IR source 10 and directed towards the IR analyser 11, as shown schematically in FIGS. 2a and 2b. Said reflector elements 3 and 3' are positioned, during the construction step, so as to orient the optical path 4 delimited towards the outside of the reflector wall 6, so as to lengthen or shorten said path; depending on the desired increased resolution and sensitivity to be achieved with reference to the target gas.

The conformation and extension of the reflector elements 3, which provide for the possibility of surfaces with different inclinations, may orient the electromagnetic radiation in as many different ways relative to the active part or relative part which the IR analyser 11 is provided with. The positioning of the reflectors 3, 3' in the body 1 may be performed by means of gluing or with attachment pins (not shown), or by shaping said reflectors (3, 3').

FIGS. 2a and 2b show two possible examples of positioning of two reflectors 3 and 3', by way of example consisting of sheets having a semicircular extension of different diameter, along the optical path comprised between the reflector wall 6 of the body 1 and the convex wall 7 of the shaped appendage 5. In particular, the reflectors 3 and 3' are respectively positioned between the reflector wall 6 of the body 1 and the convex wall 7 of the shaped appendage 5, as well as between said reflector wall 6 of the body 1 and the concave wall 7' of the shaped appendage.

Figure 4A:
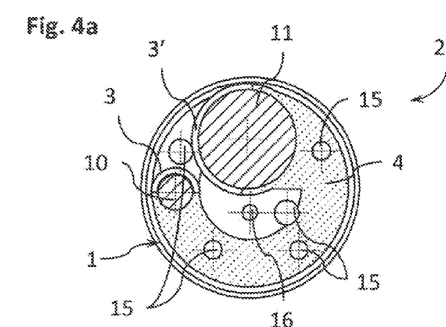
Figure 4B:
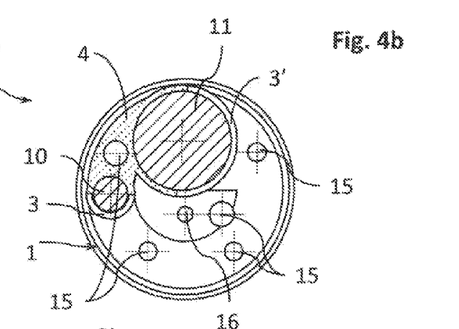
Figure 4C:
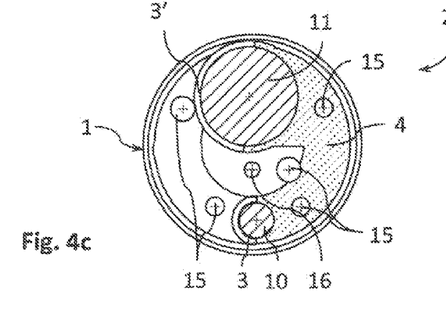
FIGS. 4c and 4d illustrate by way of example, two further alternatives, intermediate as regards the extension of the optical path made inside the detector, deriving from a different positioning of the reflector and the IR source in the body.
Figure 4D:
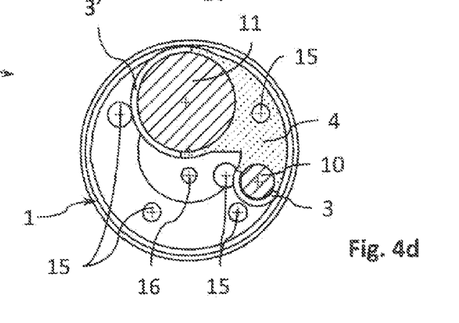

The respective optical paths 4 have significantly different lengths, the more so in the solution in FIG. 2b. For greater clarity, the optical path 4 of the electromagnetic radiation is shown in FIGS. 4a and 4b in a plan view highlighted by dots, in the presence of the same arrangement of the reflectors 3 indicated in FIGS. 2a and 2b; it can be seen that the path in figure FIG. 4a, comprising the two reflectors 3, is decidedly longer than that shown in FIG. 4b. In the same way, FIGS. 4c and 4d propose, by way of example, two further alternatives, intermediate as regards the extension of the optical path 4, deriving from a different positioning of the reflector 3 and the IR source 10 in the body 1.

Figure 5:
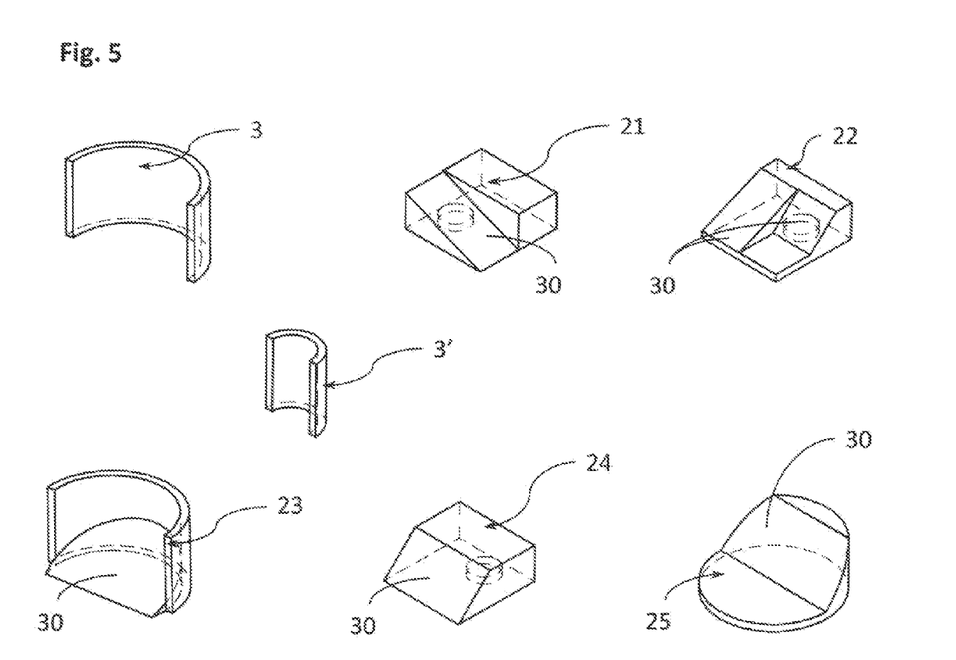
FIG. 5 is a schematic view of some types of reflector elements which are placed inside the body of said detector.

Said reflectors may be configured differently from those 3, 3' of the examples as per the aforementioned figures and provide, for example, for conformations such as those illustrated prospectively in FIG. 5, wherein such reflectors consist of irregular prismatic bodies, or of a plate shaped with a circular layout, or by an analogous plate with an inclined plane at the base and are indicated by reference numerals 21, 22, 23, 24, 25; the same figure schematically also represents the reflectors 3 and 3' mentioned.

The reflectors from 21 to 25 have at least one inclined wall 30 which appropriately deviates the electromagnetic radiation in output from the IR source 10 or in input to the IR 11 analyser; in the same way as the reflectors 3, 3', the reflectors 21 to 25 are alternatively pre-configured and attached in the body 1 during the construction step, according to the specific needs, by means of gluing or pins.

Figure 6A:
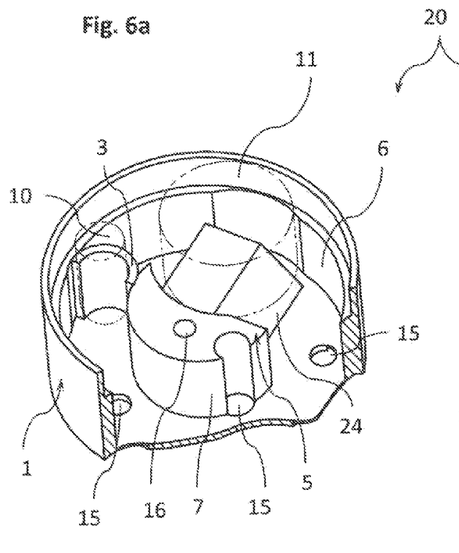
FIGS. 6a and 6b are schematic, axonometric views partially in cross-section, of two different optical path geometries realisable with the insertion of various reflector elements.
Figure 6B:
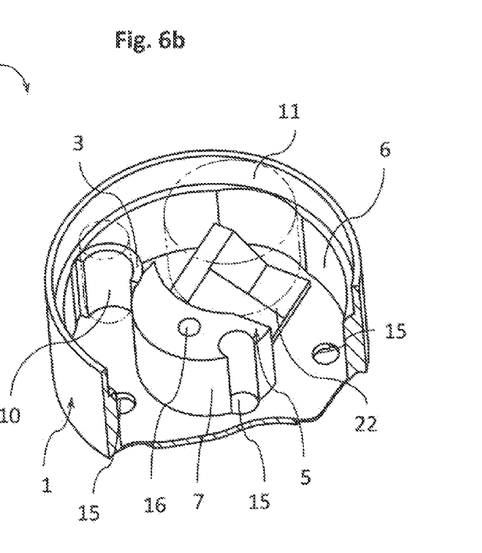

FIGS. 6a and 6b schematically represent an alternative embodiment of the optical detector according to the present invention, wherein a reflector 3 combined with a reflector 24 (in FIG. 6a) and with a reflector 22 (in FIG. 6b) is positioned in the body 1; this makes it possible to aim beams of electromagnetic radiation of different intensity onto specific pre-defined parts of the IR analyser 11 depending on the type and the concentration of the gas to be detected. The functioning of the variable geometry optical gas detector may be inferred from a description of the parts composing it. The IR source 10 emits the electromagnetic radiation which proceeds inside the optical path 4, bouncing off the reflector surfaces composed of the reflector wall 6 of the body 1 and of the convex and concave walls 7 and 7' of the outer surface of the shaped appendage 5 and which delimit said optical path.

A target gas of the detection which is present in the atmosphere enters the body 1 through the through holes and is diffused inside the optical path 4. The presence of the gas to be detected absorbs part of the electromagnetic radiation, attenuating it or altering its characteristics. This attenuation and alteration is detected by the IR analyser 11 which perceives the presence of the gas. As may be inferred from the description, the accuracy and precision of detection of the target gas depends on the geometry and greater or lesser extension of the optical path 4 within which such gas is diffused, combined with one or more types of the reflectors mentioned. In fact such geometry, to be optimal, is related to the type of gas to be sought.

As shown by way of example in FIGS. 4a and 4b, the different arrangement of the reflectors 3,3' in fact creates alternative optical paths 4 of different lengths and utilisable depending on the nature of the gas to be sought.

FIGS. 7a and 7b show two embodiments wherein the reflector wall 6 has an irregular, closed extension with tendentially straight or arched sections 32, forming areas with a concave, convex or mixed-linear extension and a corresponding optical path 4 more extensive than a circular extension.

In said figures, the shaped appendage 5 has, along its perimeter, two reflector walls 33 having a rectilinear or orthogonal extension to each other. The reflectors in FIG. 7a are of the type indicated by way of example by reference numeral 24 in FIG. 5, while in FIG. 7b they are of the type indicated by reference numerals 21 and 25 in the same figure.

The possibility of positioning the IR source 10 in alternative points, makes it possible to further broaden the possible geometric configurations and optimal extensions of the optical detector which the present invention relates to, making it versatile and applicable for the detection of multiple types of gaseous substances.

From the description of the functioning it can be seen how the variable geometry optical gas detector proves particularly advantageous and preferable in that with the use of a single body and the configuration of a few standardised elements it makes it possible to create a multiplicity of specially calibrated sensors predisposed for accurately and precisely detecting a particular type of gas.

The possibility of making the radiation cover a two-way path and thus reach the IR analyser 11 from two directions having optical paths 4 of a different shape and length guarantees the detector according to the invention increased accuracy and measuring precision, as well as a de facto increase in the range of concentrations of detectable gases.

Despite the invention having been described above with particular reference to one of its embodiments, given solely by way of a non-limiting example, numerous modifications and variants will appear evident to a person skilled in the art in the light of the above description.

The present invention therefore sets out to embrace all the modifications and variants which fall within the sphere and scope of the following claims.

The invention claimed is:

1. An optical gas detector (20) in metal, comprising:
   a cup-shaped body (1), with upper mouth (9) closed by a disc-shaped lid (2) and a bottom (8) of which is flat and provided with a plurality of through holes (15) variously arranged, which place said optical gas detector (20) in communication with an outside environment;
   an IR source (10) and an IR analyser (11), borne by an overlying circuit board (12), the IR source (10), IR analyser (11), and circuit board (12) placed within said cup-shaped body (1),
   wherein an inner lateral surface of the said cup-shaped body (1) has an annular extension comprising one or more sections (32) of a first reflector wall (6);
   the optical gas detector (20) further comprising:
   a second reflector wall (7, 7') of a shaped appendage (5) placed within the cup-shaped body (1);
   one or more additional reflectors (3, 3', 21, 22, 23, 24, 25); and
   housings or reference marks provided within the cup-shaped body (1) for the placement during construction and assembly of the one or more additional reflectors 3 3' 21 22 23 24 25), the housing or reference marks corresponding in size and shape to the one or more reflectors (3, 3', 21, 22, 23, 24, 25);
   wherein during construction and assembly the IR source 10 is mounted in one of a plurality of predetermined positions, and the one or more additional reflectors (3, 3', 21, 22, 23, 24, 25) is positioned in the housing or reference marks, such that the alternative configurable positions of said IR source (10) within said cup-shaped body (1) and alternative configurable positions of said one or more additional reflectors (3, 3', 21, 22, 23, 24, 25), produces a multiplicity of different alternative lengths of optical paths (4) of the electromagnetic radiation emitted by the IR source (10) and detected by the IR analyser (11).

2. The optical gas detector (20) according to claim 1, characterised in that said one or more additional reflectors (3, 3', 21, 22, 23, 24, 25) diversely positioned and oriented, are positioned between said first reflector wall (6) of said cup-shaped body (1) and a convex or concave second reflector wall (7, 7') of said shaped appendage (5) and delimit a different optical path (4) of the electromagnetic radiation defining the extension and geometry thereof.

3. The optical gas detector according to claim 1, characterised in that said shaped appendage (5) comprises two reflector walls (33) having a rectilinear extension directed orthogonally to each other which close the optical path (4) of the electromagnetic radiation.

4. The optical gas detector (20) according to claim 1, characterised in that the cup-shaped body (1) is closed above by said disc-shaped lid (2) provided with through apertures (10') and (11') in which said IR source (10) and IR analyser (11) are inserted, entirely or partially and attached with screws to said lid (2), said IR source (10) and IR analyser (11) extending below into the cup-shaped body (1).

5. The optical gas detector (20) according to claim 1, characterised in that said lid (2) is inserted through the upper mouth (9) and attached by means of screws or equivalent in the hole (16) of the cup-shaped body (1) and abuts at a recess (9') extending annularly in said cup-shaped body (1) and constituting the upper rim of the first reflector wall (6).

6. The optical gas detector (20) according to claim 1, characterised in that the one or more additional reflectors (3, 3', 21, 22, 23, 24, 25) comprise a semi-circular sheet, said reflector (23) being provided with a plane inclined at the base (30).

7. The optical gas detector (20) according to claim 1, characterised in that the one or more additional reflectors (3, 3', 21, 22, 23, 24, 25) comprise at least one inclined plane (30).

8. The optical gas detector (20) according to claim 1, characterised in that said inner lateral surface defining the first reflector wall (6) of said cup-shaped body (1) defines a circular regular extension.

9. The optical gas detector (20) according to claim 1, characterised in that the inner lateral surface defining the first reflector wall (6) of the cup-shaped body (1) defines an annular irregular extension, being said one or more sections (32) rectilinear or arched shaped and alternating with each other to form areas having a concave, convex or mixed-linear extension.

* * * * *